United States Patent [19]

Weyn et al.

[11] 4,357,317

[45] Nov. 2, 1982

[54] DENTAL CREAM COMPOSITION

[75] Inventors: Hendrik F. Weyn, Embourg, Belgium; Eric Baines, Flixton; Kenneth Harvey, Wilmslow, both of England

[73] Assignee: Colgate-Palmolive Company, New York, N.Y.

[21] Appl. No.: 219,298

[22] Filed: Dec. 22, 1980

[30] Foreign Application Priority Data

Dec. 19, 1979 [GB] United Kingdom ............... 7943642

[51] Int. Cl.$^3$ .......................... A61K 7/16; A61K 7/18
[52] U.S. Cl. ...................................... 424/52; 424/49; 424/57
[58] Field of Search .................................... 424/52, 57

[56] References Cited

U.S. PATENT DOCUMENTS

| | | | |
|---|---|---|---|
| 3,308,029 | 3/1967 | Saunders et al. | 424/52 |
| 3,634,585 | 1/1972 | Manahan et al. | 424/52 |
| 3,699,220 | 10/1972 | Westrate et al. | 424/52 |
| 3,927,202 | 12/1975 | Harvey et al. | 424/57 |
| 3,959,458 | 5/1976 | Agricola et al. | 424/52 |
| 4,098,878 | 7/1978 | Baines et al. | 424/52 |
| 4,152,419 | 5/1979 | Pensak | 424/52 |

FOREIGN PATENT DOCUMENTS

| | | |
|---|---|---|
| 1965046 | 7/1971 | Fed. Rep. of Germany . |
| 2135257 | 12/1972 | France . |
| 376169 | 5/1975 | Sweden . |
| 1435624 | 5/1976 | United Kingdom . |
| 1514942 | 6/1978 | United Kingdom . |
| 1544537 | 4/1979 | United Kingdom . |

OTHER PUBLICATIONS

J. Soc. Cosmet. Chem., vol. 25, pp. 3-11, (1974), Noren et al.
Extrait de L'Information Dentaire, No. 25, Jun. 18, 1970, Held et al.
New Zealand Dental Journal, vol. 70, pp. 98-108.

Primary Examiner—Shep K. Rose
Attorney, Agent, or Firm—Robert L. Stone; Murray M. Grill; Herbert S. Sylvester

[57] ABSTRACT

A dental cream composition containing a binary fluorine providing system which provides about 1000-1670 ppm (0.1-0.16% by weight) fluorine from sodium monofluorophosphate and sodium fluoride wherein sodium fluoride provides about 30-35% by weight of the fluorine in amount of about 300-580 ppm (0.02-0.058% by weight). The dental cream contains a vehicle for the binary fluorine-providing system and about 20-75% by weight of a dentally acceptable water-insoluble polishing agent consisting essentially of dicalcium phosphate intimately dispersed in the vehicle and in direct contact with the binary fluorine-providing system. The dental cream is effective in retaining soluble fluorine and soluble fluoride, in effecting reduction of enamel solubility and in remineralization of dental enamel.

7 Claims, No Drawings

DENTAL CREAM COMPOSITION

This invention relates to a dental cream composition for promotion of oral hygiene, for example for reducing caries formation and enamel solubility and for promotion of remineralisation of dental enamel which has been demineralised.

Dental cream containing sodium monofluorophosphate and dicalcium phosphate is effective in reducing formation of dental caries. It is also desirable that a dental cream promotes remineralisation of dental enamel. To this end, in accordance with the present invention, the dental cream containing sodium monofluorophosphate is modified to incorporate therein a single additional fluorine-containing component, i.e. sodium fluoride, in amount and ratio with regard to sodium monofluorophosphate indicated below. It is quite unexpected that such a dental cream would provide improvements in promotion of oral hygiene since sodium fluoride is incompatible with dicalcium phosphate, (dihydrate, anhydrous or mixtures thereof). However, it does indeed reduce caries formation by effecting a high level of fluoride "uptake" into dental enamel, reducing enamel solubility and promoting remineralisation.

Furthermore, prior art relative to dental creams containing a mixture of sodium monofluorophosphate and sodium fluoride does not lead one skilled in the art to the present invention.

British Pat. No. 1,514,942 to Forward et al (Beecham Group) describes an oral hygiene composition containing an ammonium salt in which a mixture of sodium monofluorophosphate and sodium fluoride may be present and in which the polishing agent could be hydrated or anhydrous dicalcium phosphate. British Pat. No. 1,435,624 to Forward (Beecham Group) describes an oral hygiene composition in which a mixture of sodium monofluorophosphate and sodium fluoride is also present and in which the dental abrasive (polishing agent) is calcium carbonate alone or in admixture with a further dental abrasive, such as hydrated or anhydrous dicalcium phosphate.

In each of the two patents discussed above the mixture of fluorine-containing materials is present in amount such that 40–80% by weight of the fluoride content is provided by the sodium fluoride. Indeed, in British Pat. No. 1,435,624 it is indicated that low amounts of sodium fluoride should be avoided since inactivation by calcium carbonate would occur up to a threshold level. On the contrary, in the present invention, sodium fluoride is present as a separate ingredient from sodium monofluorophosphate in amount corresponding to only about 30–35% by weight of the fluorine content of the toothpaste.

U.S. Pat. No. 4,098,878 to Baines et al. (Colgate-Palmolive) teaches in Examples 6 and 7 thereof dentifrices containing sodium monofluorophosphate and sodium fluoride and dicalcium phosphate dihydrate abrasive encapsulated in stearic acid. In the present invention it has been found that dicalcium phosphate can provide improved dental hygiene even when it is intimately mixed in the dental cream vehicle with the two fluorine-containing compounds, and this in spite of the incompatibility of sodium fluoride and dicalcium phosphate.

British Pat. No. 1,544,537 to Baines et al (Colgate-Palmolive) discloses dentifrices containing sodium monofluorophosphate and sodium fluoride with alumina trihydrate polishing material which has had its surface modified. One of the modifying agents may be dicalcium phosphate. However, as a surface-modifying agent it can only comprise a small amount of the dentifrice of this patent and not the amount of 20–75% by weight which characterises the present invention.

U.S. Pat. No. 4,152,419 to Pensak (Colgate-Palmolive) discloses a dentifrice composition containing a mixture of sodium monofluorophosphate and sodium fluoride and an insoluble sodium monophosphate polishing agent. A minor amount of dicalcium phosphate (up to about 12% by weight of the total polishing material) may also be present. The fluoride retention results set forth in this patent are synergistic, beyond what would be expected from dicalcium phosphate being compatible with each of sodium monofluorophosphate and sodium fluoride separately. This is quite different from the present invention since an improvement in oral hygiene would not be expected with sodium fluoride, as the only fluoride compound present, owing to the incompatibility with dicalcium phosphate.

U.S. Pat. No. 3,959,458 to Agricola et al (Procter & Gamble) discloses compositions containing various phosphorus-containing anticalculus agents and sodium monofluorophosphate which are compatible with cosmetic silicate fillings, such as may be used on front teeth. Dicalcium phosphate is one of many possible abrasives mentioned. It is set forth that an additional material which provides fluoride ions in water, such as sodium fluoride may be present. However, fluoride from sodium fluoride is said to be present in an amount less than about 300 ppm of free fluoride ions in order to avoid damage to silicate fillings by the composition comprising the phosphorus-containing anticalculus agent. In the present invention, the amount of fluoride provided by sodium fluoride is about 300–580 ppm.

Swedish Pat. No. 376,169 (Astra Chemical Products) describes a dentifrice containing calcium monofluorophosphate and dicalcium phosphate. There may be 0.1% fluorine from calcium monofluorophosphate (1000 ppm) or up to half of the fluorine (500 ppm) may be replaced by sodium fluoride and/or sodium monofluorophosphate. Thus, the total system with three fluorine-containing compounds does not provide more than 500 ppm fluorine from sodium fluoride and sodium monofluorophosphate. This is quite different from the dental cream of the present invention in which a binary fluorine-containing system of sodium monofluorophosphate and sodium fluoride provides about 1000–1670 ppm of fluorine.

Further disclosures in the prior art of oral compositions containing sodium monofluorophosphate and sodium fluoride but which differ substantially from the present invention occur in Journal of the Society of Cosmetic Chemistry, Volume 25, pages 3–11 (1974), "The Stability of the Monofluorophosphate and Fluoride Ions in Dentifrice Containing Calcium Carbonate" by Norén et al (dicalcium phosphate is not disclosed); Extrait de L'Information Dentaire, No. 25 (June 18th, 1970), "Contribution A L'Etude de L'Eficacité de Dentifrices Fluores" by Held et al. (calcium carbonate and silica polishing agents); New Zealand Dental Journal, Volume 70, pages 98–108 (April, 1974), "A Laboratory Evaluation of New Zealand Fluoride Toothpastes" by Pearce (ionised fluoride content inherent in sodium monofluorophosphate toothpastes, no separately added fluoride; and U.S. Pat. No. 3,927,202 to Harvey et al. (Colgate-Palmolive), German U.S. Pat. No. 19 65 046 to Rau (Blendax-Werke) and French Pat. No. 2,135,257 (Blendax-Werke), each with incidental disclosures of mixed fluorine-containing compounds with no disclosures of dicalcium phosphate.

In accordance with certain of its aspects the invention relates to a dental cream composition comprising a dental vehicle, a binary fluorine-providing system which provides about 1000–1670 ppm fluorine from sodium monofluorophosphate and sodium fluoride wherein said sodium fluoride provides about 30–35% by weight of the fluorine in amount of about 300–580 ppm and intimately dispersed in said vehicle and in direct contact with said binary fluorine-providing system components about 20–75% by weight of a dentally acceptable water-insoluble polishing material consisting essentially of dicalcium phosphate.

It is an advantage of this invention that a dental cream which is effective in reducing caries formation and the solubility of dental enamel in acid is provided. It is a further advantage that remineralisation of dental enamel is promoted and a high degree of fluoride "uptake" into dental enamel is provided. Other advantages of this invention will be apparent from consideration of the disclosure.

Sodium monofluorophosphate is used in amount to provide about 700–1090 ppm fluorine to the dental cream in which the total amount of fluorine is about 1000–1670, with about 30–35% by weight to the total fluorine being provided by sodium fluoride (about 300–580 ppm). This corresponds to about 0.5–1.2% by weight of sodium monofluorophosphate and about 0.06–0.11% by weight of sodium fluoride. Preferably, the dental cream contains about 1000–1500 ppm, most preferably, about 950–1000 ppm fluorine provided by sodium monofluorophosphate and about 450–500 ppm provided by sodium fluoride.

Sodium monofluorophosphate, $Na_2PO_3F$, which, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of about 12%, preferably above 12.7%, a content of not more than 1.5%, preferably not more than 1.2% of free sodium fluoride; and a sodium monofluorophosphate content of at least 12%, preferably at least 12.1% all calculated as fluorine.

As indicated above, sodium fluoride is present as a separate fluorine-containing component from sodium monofluorophosphate. About 300–580 ppm of fluorine is provided to the dental cream by sodium fluoride.

The dental cream contains about 20–75% by weight, preferably about 40–55% of a dentally acceptable water-insoluble polishing material which consists essentially of dicalcium phosphate. Dicalcium phosphate may be employed in its dihydrated or anhydrous forms or as mixtures thereof in any desired ratio. It is preferably the sole polishing agent, but if desired minor amounts (e.g. up to about 5% by weight of the dental cream and up to about 12% by weight of the total polishing material) of other dentally acceptable water-insoluble polishing agents which do not substantially interfere with the ability of the composition of the invention to promote oral hygiene may be present. Typical polishing agents are alumina, silica, sodium aluminosilicate etc. A minor amount of hydrated alumina (e.g. about 1%) also inhibits or even eliminates the tendency of some dental creams to separate or "bleed" in their tubes.

The binary fluoride system (sodium monofluorophosphate and sodium fluoride) and polishing material are intimately dispersed in the dental vehicle and in direct contact with each other therein.

In the dental cream formulation the liquids and solids should be proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a humectant or binder such as glycerine or sorbitol. It is preferred to use glycerine. The total liquid content will generally be about 20–75% by weight of the formulation. It is preferred to use also a gelling agent in dental creams such as the natural and synthetic gum and gum-like material, e.g., Irish moss, gum tragacanth, sodium carboxymethylcellulose, polyvinylpyrrolidone and starch. Further gelling agents include water soluble, hydrophilic colloidal carboxyvinyl polymers, such as those sold under the trademark Carbopol 934 and 940 and synthetic inorganic silicated clays such as those sold under the trademark Laponite. The gelling agent content is generally up to about 10% and preferably about 0.5–5% by weight of the dental cream.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g., sodium lauryl sulphate), alkyl aryl sulphonate (e.g., sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Various other materials may be incorporated in the dental creams of this invention. Examples thereof are colouring or whitening agents, preservatives, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzyhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitably, flavour and sweetening agent may together comprise from about 0.01 to 5% or more of the instant invention.

The dental creams should have a pH practicable for use. A pH range of 5 to 9 is particularly desirable. The reference to the pH is meant to be the pH determination directly on the toothpaste. If desired, materials such as benzoic acid or citric acid may be added to adjust the pH to say 5.5 to 6.5.

The dental cream is typically packaged in an extrudible tube, such as unlined aluminium or lead, or in a pressurised container.

The following specific example further illustrative of the nature of the present invention, but it is to be understood that the invention is not limited thereto. The compositions are prepared in the usual manner and all amounts of the various ingredients are by weight unless otherwise specified.

EXAMPLE

The following dental creams are prepared by conventional dental cream formulation technique and evaluated with regard to effects in promoting dental hygiene:

|  | A(%) | B(%) | C(%) | D(%) | E(%) |
|---|---|---|---|---|---|
| Glycerol | 22.00 | 22.00 | 22.00 | 22.00 | 22.00 |
| Sodium Carboxymethyl Cellulose | 1.10 | 0.90 | 1.10 | 1.10 | 0.90 |
| Sodium Saccharin | 0.20 | 0.20 | 0.20 | 0.20 | 0.20 |
| Tetrasodium pyrophosphate | — | 0.50 | — | — | 0.50 |
| Benzoic acid | 0.20 | — | 0.30 | 0.20 | — |
| Water | 22.20 | 25.24 | 21.24 | 21.38 | 25.28 |
| Sodium monofluorophosphate | — | 0.76 | 0.76 | 0.82 | 0.82 |
| Sodium fluoride | — | 0.10 | 0.10 | — | — |
| Dicalcium phosphate dihydrate | — | 48.00 | — | — | 48.00 |
| Hydrated alumina (Alcoa 333) | 52.00 | — | 52.00 | 52.00 | — |
| Sodium lauryl sulphate | 1.50 | 1.50 | 1.50 | 1.50 | 1.50 |
| Flavour | 0.80 | 0.80 | 0.80 | 0.80 | 0.80 |

All parts percentage by weight.

Dental creams A (non-fluoride placebo with hydrated alumina); B (binary fluorine providing system with dicalcium phosphate in accordance with the present invention); C (binary fluorine providing system with hydrated alumina); and D (sodium monofluorophosphate with hydrated alumina) are evaluated for retention of soluble fluorine and soluble fluoride ion at room temperature with the following results:

TABLE 1

| Dental cream | Initial | 1 month | 3 months | 6 months | 1 year | 2 years |
|---|---|---|---|---|---|---|
| Soluble fluorine in ppm | | | | | | |
| A | 0 | 0 | 0 | 0 | 0 | 0 |
| B | 1130 | 990 | 870 | 710 | 640 | 420 |
| C | 1210 | 1110 | 1040 | 960 | 900 | 800 |
| D | 890 | 820 | 740 | 650 | 630 | 450 |
| Soluble fluoride ion in ppm | | | | | | |
| A | 0 | 0 | 0 | 0 | 0 | 0 |
| B | 220 | 200 | 160 | 160 | 160 | 180 |
| C | 250 | 180 | 190 | 24 | 22 | 300 |
| D | 50 | 40 | 100 | 110 | 70 | 120 |

Dental creams B, C, D and E (sodium monofluorophosphate and dicalcium phosphate) are subjected to an enamel solubility reduction to determine solubility of enamel contacted with a buffered acid and each dental cream with the following results:

TABLE II

| Dental Creams | Percent of enamel solubility reduction |
|---|---|
| B | 12.7 |
| C | 23.4 |
| D | 3.7 |
| E | 1.4 |

Dental creams B, C and D are compared with a control of distilled water to determine in vitro remineralisation of dental enamel with the following results:

TABLE III

| Composition | Mean Percent Remineralisation |
|---|---|
| Distilled Water | −3.3 |
| Dental Cream | |
| B | +12.7 |
| C | −16.4 |
| D | −23.7 |

The uptake of fluoride ion by dental enamel with dental creams A, B, C and D is determined with the following results on 10 thin enamel layers of bovine incisors (the depth of each layer in millimicrons is indicated in parenthesis below the fluoride uptake figures):

TABLE IV

| Dental Creams | Fluoride uptake in ppm layer — Layer Number | | | | | | | | | |
|---|---|---|---|---|---|---|---|---|---|---|
| | 1 | 2 | 3 | 4 | 5 | 6 | 7 | 8 | 9 | 10 |
| A | 66 | 52 | 36 | 27 | 23 | 19 | 19 | 17 | 15 | 15 |
| | (6.6) | (21.3) | (38.1) | (55.6) | (72.8) | (89.3) | (104.4) | (118.5) | (132.6) | (146.7) |
| B | 512 | 1086 | 1410 | 980 | 453 | 238 | 126 | 72 | 47 | 35 |
| | (5.5) | (17.8) | (31.7) | (46.3) | (62.2) | (78.5) | (95.0) | (111.4) | (128.2) | (145.0) |
| C | 434 | 1007 | 941 | 522 | 252 | 122 | 65 | 42 | 33 | 28 |
| | (6.4) | (20.5) | (36.4) | (53.1) | (70.2) | (87.5) | (104.4) | (121.2) | (137.9) | (154.3) |
| D | 668 | 1173 | 960 | 545 | 244 | 120 | 62 | 40 | 31 | 24 |
| | (6.7) | (21.0) | (37.1) | (53.5) | (69.8) | (86.8) | (104.0) | (121.2) | (138.3) | (155.3) |

It is noted that fluoride uptake found with placebo dental cream A would be due to fluoride independently present in the dental enamel enamel.

Soluble fluorine and soluble fluoride ion levels (Table I) are determined by routine laboratory techniques.

Enamel solubility evaluations (Table II) are determined on enamel powdered from extracted human teeth with enamel separated from dentine. Dental cream solutions are contacted with the powdered enamel and then after drying the enamel is etched with a buffered acid solution. The percent of reduction in enamel solubility is determined by comparison of the amount enamel contacted with test dental creams in comparison to a control which is dissolved.

Remineralisation evaluations (Table III) are determined with human intact premolars which are first demineralised on a portion of the teeth with a buffered acid gel. To determine the amount of mineral removed from a sample tooth a portion of the demineralised surface of the remaining teeth are then treated with a control solution or slurries of the test dental creams.

Fluoride uptake evaluations (Table IV) are determined on blocks of cleaned bovine incisors which are immersed in an acid buffered solution containing hydroxyapatite and stirred for one hour at 37° C. with slurries of the test dental creams. The dental creams are then removed from demineralised white spot blocks and placed in a metastable solution of simulated saliva to eliminate unreacted fluoride. Ten thin enamel layers are removed from the blocks of bovine enamel and the depths of each level and fluoride content of each level determined.

The results set forth in Tables I–IV show that while dental creams B, C and D effectively retain desirable levels of soluble fluorine and soluble fluoride ion upon aging (Table I) only dental creams B and C reduce solubility of dental enamel in comparison with dental creams D and E (Table II) and only dental cream B promotes remineralisation in comparison with dental creams C and D (Table III) and dental cream B is generally more effective in promoting fluoride uptake of dental enamel than dental creams C and D, particularly in the deeper (3–10) layers (Table IV).

We claim:

1. A dental cream composition comprising a dental vehicle, a binary fluorine providing system which provides about 0.1–0.167% by weight fluorine from sodium monofluorophosphate and sodium fluoride wherein said sodium fluoride provides about 30–35% by weight of the fluorine in amount of about 0.03–0.058% by weight and intimately dispersed in said vehicle, and in direct contact with said binary fluorine-providing system components about 20–75% by weight of a dentally acceptable water-insoluble polishing material consisting essentially of dicalcium phosphate.

2. The dental cream composition claimed in claim 1 wherein about 0.1–0.15% by weight of fluoride is provided to said dental cream from said binary fluorine-providing system.

3. The dental cream composition claimed in claim 2 wherein about 0.09–0.1% by weight fluorine are provided by sodium monofluorophosphate and about 0.045–0.05% by weight are provided by sodium fluoride.

4. The dental cream composition claimed in claim 1 wherein about 40–55% of said polishing material is present.

5. The dental cream composition claimed in claim 4 wherein dicalcium phosphate is the only polishing agent present.

6. The dental cream claimed in claim 5 wherein there is present about 0.76% by weight of sodium monofluorophosphate, about 0.1% by weight of sodium fluoride and about 48% by weight of dicalcium phosphate dihydrate.

7. A process for promoting oral hygiene including remineralizing demineralized dental enamel comprising applying to dental enamel a dental cream composition comprising a dental vehicle, a binary fluorine providing system which provides about 0.1–0.167% fluorine from sodium monofluorophosphate and sodium fluoride wherein said sodium fluoride provides about 30–35% by weight of the fluorine in amount of about 0.03–0.058% and intimately dispersing in said vehicle for contact with said binary fluorine-providing system components, about 20–75% by weight of a dentally acceptable water-insoluble polishing material consisting essentially of dicalcium phosphate.

* * * * *